(12) United States Patent
Razavi et al.

(10) Patent No.: US 10,105,077 B2
(45) Date of Patent: Oct. 23, 2018

(54) METHOD AND SYSTEM FOR CALCULATING STRAIN FROM CHARACTERIZATION DATA OF A CARDIAC CHAMBER

(71) Applicant: Pacesetter Inc., Sunnyvale, CA (US)

(72) Inventors: Hoda Razavi, San Jose, CA (US); Kyungmoo Ryu, Palmdale, CA (US); Yelena Nabutovsky, Mountain View, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 764 days.

(21) Appl. No.: 14/270,186

(22) Filed: May 5, 2014

(65) Prior Publication Data

US 2015/0313480 A1 Nov. 5, 2015

(51) Int. Cl.
| | | |
|---|---|---|
| A61B 5/11 | (2006.01) | |
| A61B 5/06 | (2006.01) | |
| G06F 19/00 | (2018.01) | |
| A61B 6/00 | (2006.01) | |
| A61B 6/12 | (2006.01) | |

(Continued)

(52) U.S. Cl.
CPC ............ *A61B 5/11* (2013.01); *A61B 5/02028* (2013.01); *A61B 5/062* (2013.01); *A61B 5/1102* (2013.01); *G06F 19/34* (2013.01); *A61B 5/042* (2013.01); *A61B 5/1107* (2013.01); *A61B 6/12* (2013.01); *A61B 6/4441* (2013.01); *A61B 6/487* (2013.01); *A61B 6/503* (2013.01); *A61B 6/504* (2013.01);

(Continued)

(58) Field of Classification Search
None
See application file for complete search history.

(56) References Cited

U.S. PATENT DOCUMENTS

| 5,391,199 A | 2/1995 | Ben-Haim |
| 5,713,367 A | 2/1998 | Arnold et al. |

(Continued)

FOREIGN PATENT DOCUMENTS

| EP | 1 070 480 A2 | 1/2001 |
| EP | 1 508 300 A1 | 2/2005 |

(Continued)

OTHER PUBLICATIONS

Denney et al. (J Magn Res Imaging (1997) vol. 7:799-810).*

(Continued)

*Primary Examiner* — Lori A. Clow
(74) *Attorney, Agent, or Firm* — Theresa A. Raymer

(57) ABSTRACT

A method and system is provided for calculating a strain from characterization motion data. The method and system utilize an intravascular mapping tool configured to be inserted into at least one of the endocardial or epicardial space. The mapping tool is maneuvered to select locations proximate to surfaces of the heart, while collecting map points at the select locations to form a point cloud data set during at least one cardiac cycle. The method and system further include automatically assigning segment identifiers (IDs) to the map points based on a position of the map point within the point cloud data set. The method and system further select a first and second reference from a group of map points. Further, the method and system calculate a linear strain based on an instantaneous distance and a reference distance between the first and second references.

20 Claims, 10 Drawing Sheets

(51) Int. Cl.
*A61B 5/02* (2006.01)
*A61B 5/042* (2006.01)

(52) U.S. Cl.
CPC ....... *A61B 6/5247* (2013.01); *A61B 2576/023* (2013.01); *G06F 19/321* (2013.01)

(56) References Cited

U.S. PATENT DOCUMENTS

| | | | |
|---|---|---|---|
| 6,233,476 | B1 | 5/2001 | Strommer et al. |
| 6,301,496 | B1 | 10/2001 | Reisfeld |
| 6,609,027 | B2 | 8/2003 | Kroll et al. |
| 6,633,686 | B1 | 10/2003 | Bakircioglu et al. |
| 6,728,562 | B1 | 4/2004 | Budd et al. |
| 6,751,492 | B2 | 6/2004 | Ben-Haim |
| 6,978,168 | B2 | 12/2005 | Beatty et al. |
| 7,197,354 | B2 | 3/2007 | Sobe |
| 7,263,297 | B2 | 8/2007 | Hauck et al. |
| 7,276,064 | B2 | 10/2007 | Paul et al. |
| 7,338,486 | B2 | 3/2008 | Sliwa et al. |
| 7,386,339 | B2 | 6/2008 | Strommer et al. |
| 7,505,809 | B2 | 3/2009 | Strommer et al. |
| 7,697,973 | B2 | 4/2010 | Strommer et al. |
| 7,881,769 | B2 | 2/2011 | Sobe |
| 8,016,764 | B1 | 9/2011 | Shelchuk |
| 8,195,292 | B2 | 6/2012 | Noren et al. |
| 8,849,381 | B2 | 9/2014 | Mason et al. |
| 9,162,067 | B1 | 10/2015 | Farazi et al. |
| 2003/0093067 | A1 | 5/2003 | Panescu |
| 2003/0233039 | A1 | 12/2003 | Shao et al. |
| 2005/0154282 | A1 | 7/2005 | Li et al. |
| 2006/0245536 | A1 | 11/2006 | Boing |
| 2007/0055142 | A1 | 3/2007 | Webler et al. |
| 2007/0073179 | A1 | 3/2007 | Afonso et al. |
| 2007/0100332 | A1 | 5/2007 | Paul et al. |
| 2007/0106146 | A1 | 5/2007 | Altmann et al. |
| 2007/0181139 | A1 | 8/2007 | Hauck |
| 2007/0190438 | A1 | 8/2007 | Kim et al. |
| 2007/0244479 | A1 | 10/2007 | Beatty et al. |
| 2007/0270705 | A1 | 11/2007 | Starks |
| 2007/0299352 | A1 | 12/2007 | Harlev |
| 2008/0009758 | A1 | 1/2008 | Voth |
| 2008/0091193 | A1 | 4/2008 | Kauphusman et al. |
| 2009/0163904 | A1 | 6/2009 | Miller et al. |
| 2009/0171345 | A1 | 7/2009 | Miller et al. |
| 2009/0275828 | A1* | 11/2009 | Shachar ............... A61B 5/0422 600/425 |
| 2009/0306732 | A1 | 12/2009 | Rosenberg et al. |
| 2010/0168550 | A1 | 7/2010 | Byrd et al. |
| 2010/0268059 | A1 | 10/2010 | Ryu |
| 2011/0190593 | A1 | 8/2011 | Mcnair et al. |
| 2011/0208038 | A1 | 8/2011 | Konofagou et al. |
| 2011/0243401 | A1 | 10/2011 | Zabair et al. |
| 2012/0184863 | A1 | 7/2012 | Harlev et al. |
| 2013/0222415 | A1 | 8/2013 | Vilsmeier |
| 2013/0272592 | A1 | 10/2013 | Eichler et al. |
| 2015/0045867 | A1 | 2/2015 | Krishnan et al. |
| 2015/0133802 | A1 | 5/2015 | Nabutovsky et al. |
| 2015/0141765 | A1 | 5/2015 | Razavi et al. |
| 2015/0141858 | A1 | 5/2015 | Razavi et al. |
| 2017/0042481 | A1 | 2/2017 | Olson |

FOREIGN PATENT DOCUMENTS

| | | |
|---|---|---|
| EP | 2 757 528 A1 | 7/2014 |
| WO | 97/24981 A2 | 7/1997 |
| WO | 2012/090148 A1 | 7/2012 |

OTHER PUBLICATIONS

Notice of Allowance dated Jun. 22, 2015; Related U.S. Appl. No. 14/328,523.
Bogatyrenko, Evgeniya et al., Efficient Physics-Based Tracking of Heart Surface Motion for Beating Heart Surgery Robotic Systems, International Journal of Computer Assisted Radiology and Surgery, vol. 6, No. 3, pp. 387-399, Aug. 2010.
International Search Report and Written Opinion in PCT Application No. PCT/US2015/028206 (dated Jul. 22, 2015).
Quatember, Bernhard et al., "Geometric Modeling and Motion Analysis of the Epicardial Surface of the Heart", Mathematics and Computers in Simulation, vol. 81, No. 3, pp. 608-622, Nov. 2010.
Segars, W. Paul et al., "A Realistic Spline-Based Dynamic Heart Phantom", IEEE Transactions on Nuclear Science, vol. 46, No. 3, pp. 503-506, Jun. 1999.
U.S. Appl. No. 09/107,371, filed Jun. 30, 1998 for "Chamber Mapping System".
Advisory Action dated Aug. 10, 2015; Related U.S. Appl. No. 12/347,216.
Amendment filed Jun. 25, 2015; Related U.S. Appl. No. 12/347,216.
Final Office Action dated May 4, 2015; Related U.S. Appl. No. 12/347,216.
Amendment filed Dec. 18, 2014; Related U.S. Appl. No. 12/347,216.
Non-Final Office Action dated Oct. 2, 2014; Related U.S. Appl. No. 12/347,216.
Advisory Action dated May 1, 2014; Related U.S. Appl. No. 12/347,216.
Amendment filed Apr. 24, 2014; Related U.S. Appl. No. 12/347,216.
Applicant Interview Summary, Apr. 21, 2014; Related U.S. Appl. No. 12/347,216.
Final Office Action dated Feb. 25, 2014; Related U.S. Appl. No. 12/347,216.
Amendment filed Feb. 4, 2014; Related U.S. Appl. No. 12/347,216.
Non-Final Office Action dated Nov. 21, 2013; Related U.S. Appl. No. 12/347,216.
Amendment filed Oct. 29, 2012; Related U.S. Appl. No. 12/347,216.
Advisory Action dated Oct. 11, 2012; Related U.S. Appl. No. 12/347,216.
Amendment filed Oct. 1, 2012; Related U.S. Appl. No. 12/347,216.
Advisory Action dated Sep. 12, 2012; Related U.S. Appl. No. 12/347,216.
Amendment filed Aug. 28, 2012; Related U.S. Appl. No. 12/347,216.
Final Office Action dated Jun. 29, 2012; Related U.S. Appl. No. 12/347,216.
Amendment filed May 14, 2012: Related U.S. Appl. No. 12/347,216.
Interview Summary, Feb. 28, 2012; Related U.S. Appl. No. 12/347,216.
Non-Final Office Action dated Feb. 13, 2012; Related U.S. Appl. No. 12/347,216.
Notice of Allowance dated Oct. 27, 2015; Related U.S. Appl. No. 14/328,523.
USPTO, "Notice Allowance for U.S. Appl. No. 14/270,176", dated May 20, 2016.
Non-Final Office Action dated Dec. 11, 2015; Related U.S. Appl. No. 14/703,760.
Non-Final Office Action dated Sep. 30, 2015; Related U.S. Appl. No. 14/270,181.
Notice of Allowance dated Dec. 8, 2015; Related U.S. Appl. No. 12/347,216.
Final Office Action dated Jan. 22, 2016; Related U.S. Appl. No. 14/270,176.
Non-Final Office Action dated Feb. 8, 2016; Related U.S. Appl. No. 14/270,181.
USPTO, "Final Office Action for U.S. Appl. No. 14/703,749", dated Jan. 23, 2017.
USPTO, "Non-Final Office Action for U.S. Appl. No. 14/703,735", dated Jan. 12, 2017.
USPTO, "Non-Final Office Action for U.S. Appl. No. 14/703,744", dated Jan. 13, 2017.
University of California, San Francisco, "History of AF Ablation", https://cardiology.ucsf.edu/care/clinical/electro/ablation_hist.html, accessed on Jan. 17, 2017. (online date—2012) : pp. 1-4.
Notice of Allowance dated Feb. 25, 2016; Related U.S. Appl. No. 14/328,513.
Notice of Allowance dated Feb. 25, 2016; Related U.S. Appl. No. 14/703,760.
Non-Final Office Action dated Mar. 28, 2016; Related U.S. Appl. No. 14/703,749.

(56) References Cited

OTHER PUBLICATIONS

Notice of Allowance dated Apr. 19, 2016; Related U.S. Appl. No. 14/270,181.
St. Jude Medical, "EnSite Velocity Cardiac Mapping System, Model EE3300, v.4," Feb. 28, 2013, 238 pages.
Notice of Allowance dated May 9, 2017; Related U.S. Appl. No. 14/703,749.
USPTO, "Non-Final Office Action for U.S. Appl. No. 14/703,757", dated Apr. 6, 2017.
USPTO, "Non-Final Office Action for U.S. Appl. No. 14/478,707", dated Mar. 2, 2017.
Office Action dated Jul. 5, 2017; Related U.S. Appl. No. 14/270,191.
Notice of Allowance dated Jun. 2, 20017; Related U.S. Appl. No. 14/703,744.
Notice of Allowance dated Oct. 2, 20017; Related U.S. Appl. No. 14/478,707.
Final Office Action dated Oct. 25, 2017; Related U.S. Appl. No. 14/270,191.
Notice of Allowance dated Nov. 29, 2017; Related U.S. Appl. No. 14/703,757.

* cited by examiner

METHOD AND SYSTEM FOR CALCULATING STRAIN FROM CHARACTERIZATION DATA OF A CARDIAC CHAMBER

RELATED APPLICATION DATA

The present application is related to the following applications: U.S. provisional application Ser. No. 61/906,311, filed Nov. 19, 2013, titled "METHOD AND SYSTEM TO ASSESS MECHANICAL DYSSYNCHRONY BASED ON MOTION DATA COLLECTED BY A NAVIGATION SYSTEM", U.S. provisional application Ser. No. 61/910,630, filed Nov. 19, 2013, titled "METHOD TO MEASURE CARDIAC MOTION USING A CARDIOVASCULAR NAVIGATION SYSTEM", U.S. provisional application Ser. No. 61/906,305, filed Nov. 19, 2013, titled "METHOD TO IDENTIFY CARDIAC CYCLES WITH CONSISTENT ELECTRICAL RHYTHM AND MECHANICAL BEHAVIOR FOR COMPILATION INTO A REPRESENTATIVE, CHARACTERIZATION OF CARDIAC MOTION", U.S. patent application titled "METHOD AND SYSTEM TO CHARACTERIZE MOTION DATA BASED ON NEIGHBORING MAP POINTS", which is filed on or about the same day as the present application, U.S. patent application titled "METHOD AND SYSTEM FOR DISPLAYING A THREE DIMENSIONAL VISUALIZATION OF CARDIAC MOTION", now U.S. Pat. No. 9,380,940, which is filed on or about the same day as the present application, and U.S. patent application titled "METHOD AND SYSTEM TO AUTOMATICALLY ASSIGN MAP POINTS TO ANATOMICAL SEGMENTS", published as U.S. Pub. No. 2015/0317448, which is filed on or about the same day as the present application, all of which are expressly incorporated herein by reference in their entirety.

BACKGROUND OF THE INVENTION

Embodiments of the present disclosure generally relate to methods and systems for cardiovascular navigation, and more particularly for calculating the strain from characterization data of a cardiac chamber or organ.

Cardiovascular navigation systems (CNS) provide real-time position and orientation information in relation to a part of the cardiovascular system, such as the heart based on sensors placed at various locations within the cardiovascular system. The CNS may be integrated with a fluoroscopic (or other diagnostic) imaging system and track the sensors continuously within an imaging volume defined by the fluoroscopic system, on both live and recorded background diagnostic images.

Recently, it has been proposed to utilize the CNS to evaluate the motion of the heart and identify a desired (e.g., optimal) location for placement of a left ventricular (LV) lead. For example, the CNS may systematically record information, such as displacement of the sensors, associated with various endocardial and epicardial locations of the LV. Epicardial locations may include mapping within the coronary sinus branches as well as mapping directly on the epicardial surface of the LV via a subxiphoid puncture technique, for example. Depending on the size of the heart and other factors during the procedure, there may be between 40 and 120 endocardial LV locations and up to 10 epicardial locations at which the CNS system obtains recordings for each patient. p Systems have been proposed to characterize the motion of the heart, specifically on the qualitative techniques of characterizing motion. However, the systems proposed thus far do not offer sufficient information about the behavior of heart wall tissue. A need remains for methods and system that can offer more information about heart wall behavior.

SUMMARY

In accordance with an embodiment herein, a method is provided for calculating a strain from characterization motion data. The method utilizes an intravascular mapping tool configured to be inserted into at least one of the endocardial or epicardial space. The mapping tool is maneuvered to select locations proximate to surfaces of the heart, while collecting map points at the select locations to form a point cloud data set during at least one cardiac cycle. The method further selects first and second reference locations from the point cloud data set. The first and second reference locations include at least a first and second map point, respectively. The method determines a reference distance between the first and second reference locations at a pre-defined temporal reference point in time, and an instantaneous distance between the first and second reference locations at a select point in time. Further, the method calculates a strain characteristic of wall tissue located between the first and second reference locations based on the instantaneous distance and the reference distance.

In an embodiment, a system for calculating a strain from 3-dimensional motion data is provided. The system comprises a data storage configured to store map points collected by an intravascular mapping tool configured to be inserted into at least one of the endocardial or epicardial space. The mapping tool is maneuvered to select locations proximate to surfaces of the heart, while collecting the map points at the select locations to form a point cloud data set during at least one cardiac cycle. The system further includes a processor. The processor is configured to determine a reference distance between first and second reference locations at a pre-defined temporal reference point in time, and an instantaneous distance between the first and second reference locations at a select point in time. The first and second reference locations include at least a first and second map point, respectively. Further, the processor is configured to automatically calculate a strain characteristic of wall tissue located between the first and second reference locations based on the instantaneous distance and the reference distance an intravascular mapping tool configured to be inserted into at least one of the endocardial or epicardial space.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

Figure 1:
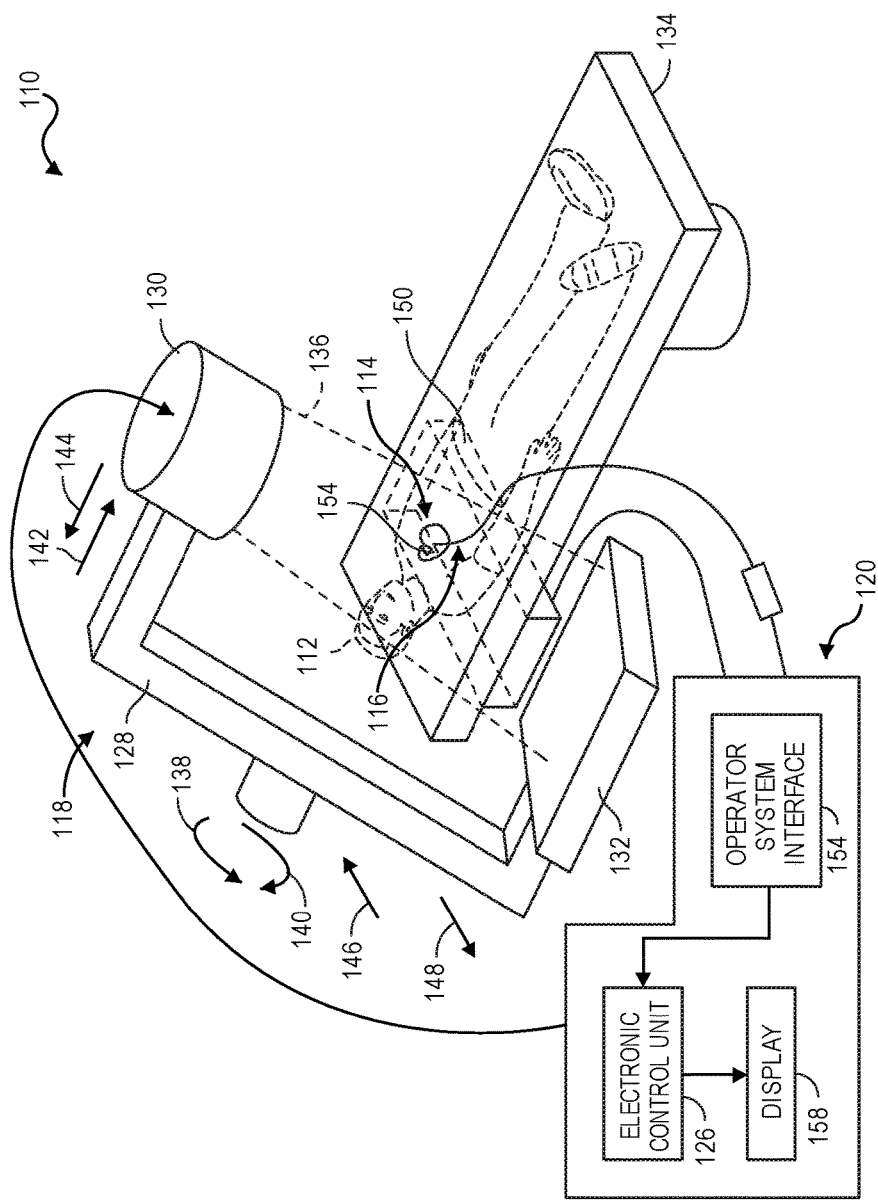
FIG. 1 illustrates a cardiovascular navigation system for use in imaging an anatomical region of the heart and to collect motion data, in accordance an embodiment herein.

FIG. 1 illustrates a cardiovascular navigation system (CNS) 110, of an embodiment, for use in imaging an anatomical region of a patient 112, such as a heart 114. A medical tool 116 is placed within the anatomical region, such as an electrophysiological (EP) mapping catheter (e.g., a guidewire) or a catheter generally described or shown in U.S. Pat. No. 7,881,769, which is expressly incorporated herein by reference. The medical tool 116 includes a plurality of electrophysiological sensors 152 that may be placed on the endocardial or epicardial surface of the left ventricle (LV) of the heart 114. The electrophysiological sensors 152 may be attached to the distal or proximal end of the medical tool 116, or any point in between. The electrophysiological sensors 152 measure a position and an electrical potential or an electric current of biological cells and tissues. The electrophysiological sensors 152 transmit the position and electrical potential information to an electronic control unit (ECU) 126. For example, the electrophysiological sensors 152 may be positioned by the medical tool 116 to measure point specific (PS) motion data for a plurality of map points of the wall of the heart 114. It should be understood, however, that the electrophysiological sensors 152 could be used in a variety of anatomical regions or alternative map points within the heart 114 or other organs in which motion characterization may be of interest. Additionally or alternatively, the electrophysiological sensors 152 may be replaced by separate motion sensors and electrical sensors. The motion sensors in contact with the region of interest (e.g., the LV of the heart 114) measure the position sensors as well as the electrical sensors that are measuring the PS motion data of the region of interest. Optionally, the ECU 126 may receive the PS motion data and electrical sensor measurements simultaneously from the motion sensors and electrical sensors.

A navigation system 120 is provided to determine the position and orientation of the medical tool 116 within the body of the patient 112. In the illustrated embodiment, the navigation system 120 comprises a magnetic navigation system in which magnetic fields are generated in the anatomical region and position sensors associated with the medical tool 116 generate an output that is responsive to the position of the sensors within the magnetic field. The navigation system 120 may comprise, for example, the systems generally shown and described in, for example, U.S. Pat. Nos. 6,233,476, 7,197,354, 7,386,339, and 7,505,809 all of which are expressly incorporated by reference in their entirety. Although a magnetic navigation system is shown in the illustrated embodiment, it should be understood that the embodiments could find use with a variety of navigation systems including those based on the creation and detection of axes specific electric fields. The navigation system 120 may include a transmitter assembly 150.

The transmitter assembly 150 may include a plurality of coils arranged orthogonally to one another to produce a magnetic field in and/or around the anatomical region of interest. It should be noted that, although the transmitter assembly 150 is shown under the body of the patient 112 and under the table 134 in FIG. 1, the transmitter assembly 150 may be placed in another location, such as attached to the radiation emitter 130, from which the magnetic field generators can project a magnetic field in the anatomical region of interest. In accordance with certain embodiments the transmitter assembly 150 is within the field of view 136. The ECU 126 may control the generation of magnetic fields by transmitter assembly 150.

The electrophysiological sensors 152 are configured to generate an output dependent on the relative position of electrophysiological sensors 152 within the field generated by the transmitter assembly 150. In FIG. 1, the electrophysiological sensors 152 and the medical tool 116 are shown disposed around the heart 114. The navigation system 120 determines the location of the electrophysiological sensors 152 within the generated field, and thus the position of the medical tool 116 as well. The navigation system 120 may further determine navigation coordinates, such as a Cartesian coordinate (e.g., (X, Y, Z)), of the navigation coordinate system.

The ECU 126 of the navigation system 120 may include or represent hardware circuits or circuitry that include and/or are connected with one or more logic based devices, such as processors, microprocessors, controllers, microcontrollers, or other logic based devices (and/or associated hardware, circuitry, and/or software stored on a tangible and non-transitory computer readable medium or memory). The ECU 126 may receive a plurality of input signals including signals generated by the medical tool 116, the electrophysiological sensors 152, an operator system interface 154 (e.g., keyboard, touchscreen, or the like), and one or more patient reference sensors (not shown) and generate a plurality of output signals including those used to control the medical tool 116 and/or the display 158. The ECU 126 may also receive an input signal from an organ monitor (not shown), such as an ECG monitor, and sort or segregate images from an imaging system 118 based on a timing signal of a monitored organ. For example, ECU 126 may sort images based on the phase of the patient's cardiac cycle at which each image was collected, as more fully described in U.S. Pat. No. 7,697,973, which is hereby incorporated by reference in its entirety.

Optionally, the CNS 110 may include an imaging system 118. The CNS 110 may further include a registration system for registering a group of images of the anatomical region of the patient 112 in a navigation coordinate system of the navigation system 120 as generally described and shown in U.S. Patent Publication 2013/0272592 and International Pub. No. WO 2012090148, the entire disclosure of which is expressly incorporated herein by reference.

Figure 5:
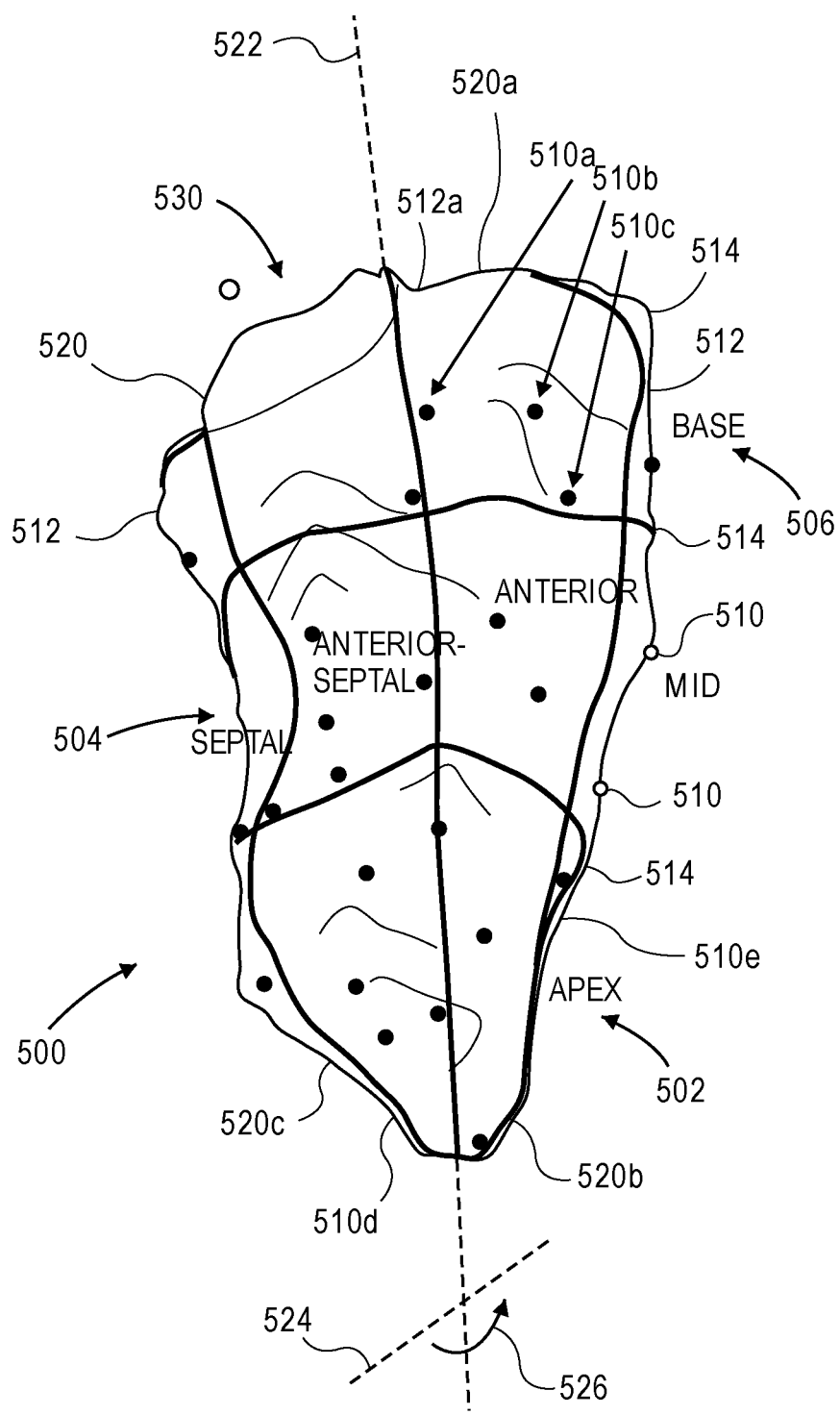
FIG. 5 illustrates map points within a segmented left ventricular in accordance with an embodiment herein.

The imaging system 118 may be provided to acquire images of the heart 114 or another anatomical region of interest (e.g., landmark points 514, 516 in FIG. 5). The imaging system 110 may, for example, comprise of a fluoroscopic imaging system. Additionally or alternatively, rather than a fluoroscopic imaging system, computed tomography (CT) imaging systems, a three-dimensional radio angiography (3DRA) system, SPECT, PET, X-ray, MR, ultrasound and the like may be used. Although the imaging system 118 is described herein for an exemplary embodiment of the invention, the imaging system 118 is not required for the inventive subject matter described within this application The imaging system 118 may include a C-arm support structure 128, a radiation emitter 130, and a radiation detector 132. The emitter 130 and detector 132 are disposed on opposite ends of the support structure 128 and disposed on opposite sides of the patient 112 as the patient 112 lays on an operation table 134. The emitter 130 and detector 132 define a field of view 136 and are positioned such that the field of view 136 includes the anatomical region of interest as the patient 112 lays on the operation table 134. The imaging system 118 is configured to capture images of anatomical features and other objects within the field of view 136. The support structure 128 may have freedom to rotate about the patient 112 as shown by lines 138 and 140. The support structure 128 may also have freedom to slide along lines 142 and 144 (e.g., along the cranio-caudal axis of the patient 112) and/or along lines 146 and 148 (e.g., perpendicular to the cranio-caudal axis of the patient 112). Rotational and translational movement of the support structure 128 yields corresponding rotational and translational movement of the field of view 136. Additionally or alternatively, the navigation system 120 may adjust the navigation coordinates of the position of the medical tool 116 to compensate for changes in the C-arm support structure 128 and respiratory movements of the patient as disclosed in the U.S. Provisional Application No. 61/910,630, entitled, "METHOD TO MEASURE CARDIAC MOTION USING A CARDIOVASCULAR NAVIGATION SYSTEM," which is expressly incorporated herein by reference in its entirety.

The imaging system 118 may acquire a group of images of an anatomical region of the patient 112 by first shifting along lines 142, 144, 146, and/or 148 to place the anatomical region of interest within the field of view 136. Second, the support structure 128 may rotate the radiation emitter 130 and the radiation detector 132 about the patient 112, keeping the anatomical region within the field of view 136. The imaging system 118 may capture images of the anatomical region as the support structure 128 rotates, providing a group of two-dimensional images of the anatomical region from a variety of angles. The group of images may be communicated to the ECU 126 for image processing and display. The group of images may comprise a sequence of images taken over a predetermined time period.

Additionally, one or more patient reference sensors (not shown) may be on the body of the patient 112, for example, on the chest. The patient reference sensors measure a displacement and orientation of the patient reference sensors relative to a predetermined reference point, such as, the electrophysiological sensors 152 or the transmitter assembly 150.

Figure 2:
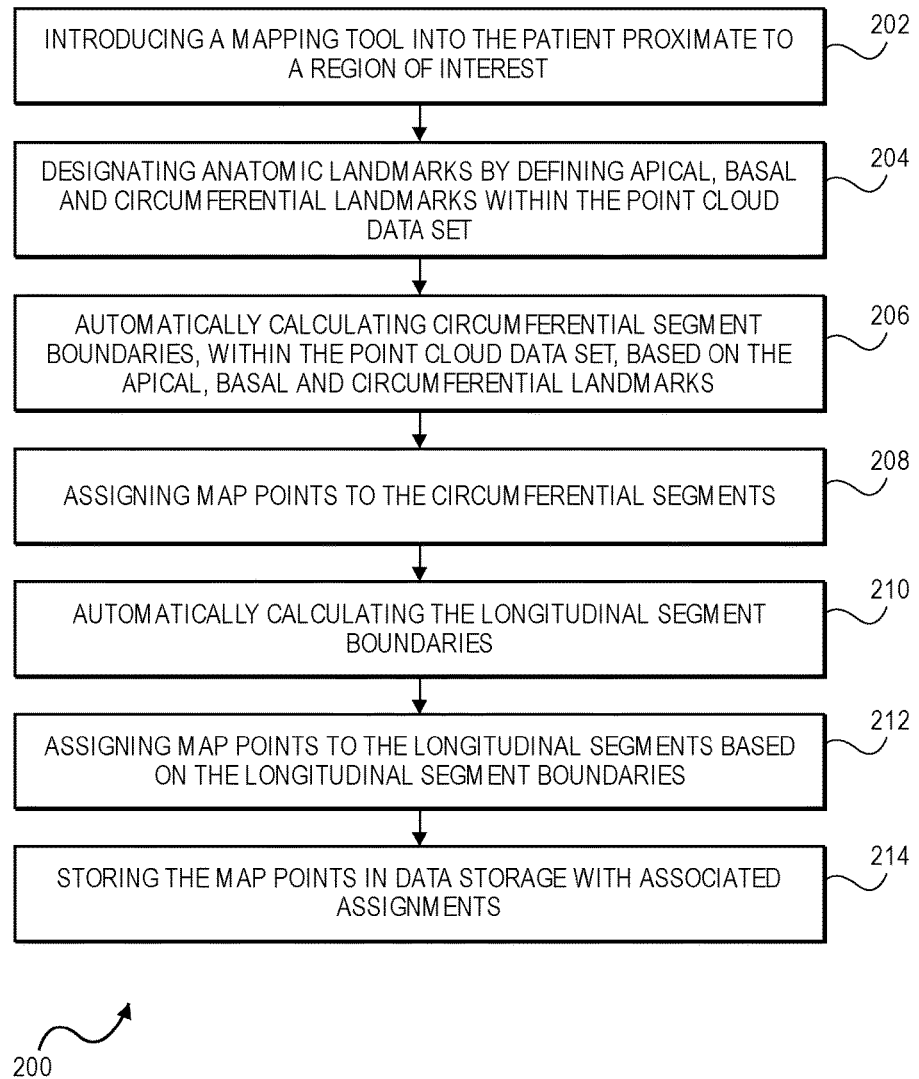
FIG. 2 illustrates a method performed in accordance with embodiments herein for assigning map points to anatomical segments of the heart.

FIG. 2 illustrates a method 200 performed in accordance with embodiments herein for assigning map points to anatomical segments of the heart. Throughout the present application, examples are provided in connection with mapping the left ventricle (LV). It should be recognized that the operations described herein may be used to map other regions of the heart. When mapping other regions of interest in the heart, different reference points and landmarks may be used.

Beginning at 202, a mapping tool (e.g., the medical tool 116) is introduced into the patient 112 proximate to a region of interest (e.g., the LV). Images are displayed to the user through the display 158. The images may be collected from various diagnostic imaging modalities (e.g. fluoroscopy, X-ray, MR, ultrasound, CT, PET, SPECT and the like) from the imaging system 118. Information from the navigation system 120, regarding the mapping tool, is combined with the images of the region of interest, and graphical representations are displayed of the mapping tool, in combination with the diagnostic image(s) on the display 158. For example, the mapping tool may be displayed superimposed upon the diagnostic image(s). By way of example, the physician may utilize intravascular mapping tool that is configured to be inserted proximate to the heart, endocardially and/or epicardially. The physician maneuvers the mapping tool between multiple locations of interest that are proximate to select areas on interior and/or exterior surfaces of the heart. For example, the physician may manipulate a mapping tool within the left ventricle and/or right ventricle to collect endocardial mapping data associated with interior surfaces of the chambers of the heart.

Figure 3:
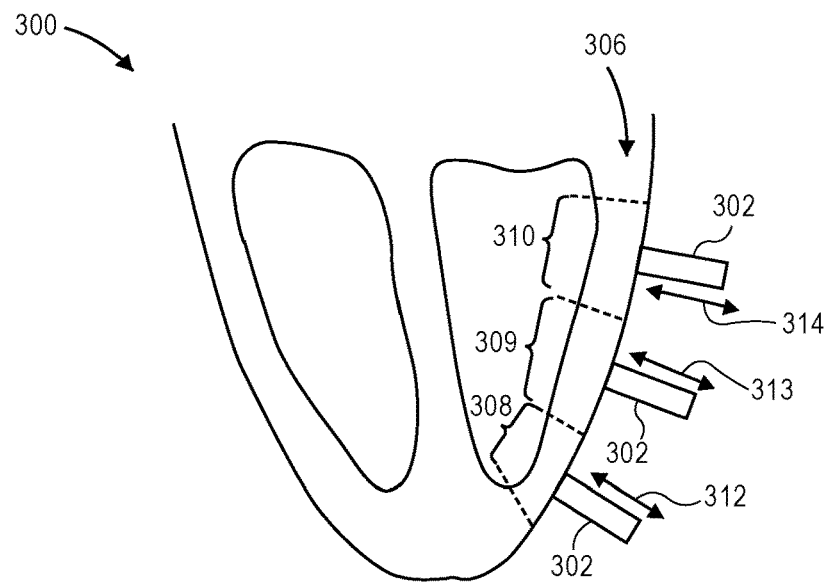
FIG. 3 illustrates a graphical representation of a plurality of map points of a heart.

Additionally or alternatively, the physician may maneuver the mapping tool along one or more veins that extend about an exterior of a select region/chamber of the heart, such as the right ventricle and/or left ventricle, to collect epicardial mapping data. For example, a medical tool 302 may acquire point specific (PS) motion data of the heart 114 at numerous map points (e.g., 308-310), positioned along the walls of the various chambers during at least one cardiac cycle. FIG. 3 illustrates a graphical representation of a plurality of map points 308-310 associated with a portion of a heart 300, such as heart wall 306, for which it is desirable to measure PS motion data. The PS motion data forms a portion of a point cloud data set. The point cloud data set may include all data collected by the medical tool 302, which may include information other than PS motion data. The term "point specific" is used to indicate that the motion data is associated with a single select location on the heart wall. The data values represent positions of the single select location over one or more cardiac cycles. The heart wall 306 may be separated or divided. The example of FIG. 3 shows three map points of interest 308-310 along the heart wall. Optionally, more or fewer map points of interest may be designated to expand the point cloud data set. The medical tool 302 (e.g., the medical tool 116 with the plurality of electrophysiology sensors 152) is positioned directly against the heart wall 306 at one or more points within each map point of interest 308-310. The tool 302 measures movement of the one or more points over a select period of time. In the example of FIG. 3, the tool 302 is shown positioned against a point of interest in each map point 308-310 at different points in time.

For example, the tool 302 is positioned, during a first measuring operation, at the map point 308 while collecting PS motion data associated with movement (e.g., along the arrow 312) by the map point 308. The movement may be in various linear, transverse, or rotational directions. The map point data is continuously or periodically collected and added to data collection, generally referred to as a point cloud data set. Next, the tool 302 may be positioned, during a second measuring operation, at the map point 309 while collecting PS motion data associated with movement (e.g., along the arrow 313) by the map point 309. Next, the tool 302 is positioned, during a third measuring operation, at the map point 310 while collecting PS motion data associated with movement (e.g., along the arrow 314) by the map point 310. The position of the tool 302 may be continuously monitored by a navigation system (e.g., the navigation system 120) to obtain sets of motion data associated with each map point 308-310 over a select period of time, such as during at least one cardiac cycle.

The point cloud data set expands over time thereby increasing an amount of information regarding the electrical and/or mechanical behavior of the region of interest within the heart. The point cloud data set is stored in a data storage (e.g., such as at a local terminal or workstation, a local area network, a wide area network, on a network, or at a remote data storage facility).

As explained herein, various analyses may be performed iteratively upon the point cloud data set throughout the data collection process. It is not necessary for a complete point cloud to be collected before analyzing the motion data.

Optionally, the navigation system 120 may perform pre-processing on the point cloud data set. For example, the CNS 110 may filter or remove PS motion data within the point cloud data set that was acquired during irregular or invalid beats (e.g., ectopic beats). The navigation system 120 may receive electrical sensor measurements of the patient 112 from a 12-lead surface electrocardiogram (ECG), body surface mapping (BSM), subcutaneous ECG, a uni- or bi-polar intracardiac electrograms (IEGMs) of a catheter, such as the medical tool 116, placed in the coronary sinus (CS), right ventricular (RV apex), or the like. The navigation system 120 may identify the invalid or irregular beats from the electrical sensor measurements and remove the invalid or irregular beats with the corresponding PS motion data subset acquired during the beat from the point cloud data set as disclosed in U.S. Provisional Application No. 61/906,305, entitled, "METHOD TO IDENTIFY CARDIAC CYCLES WITH CONSISTENT ELECTRICAL RHYTHM AND MECHANICAL BEHAVIOR FOR COMPILATION INTO A REPRESENTATIVE CHARACTERIZATION OF CARDIAC MOTION," which is expressly incorporated herein by reference in its entirety.

Optionally, the navigation system 120 may adjust PS motion data within the point cloud data set based on motion waveforms (e.g., the motion waveform 402) that correspond to the motion of a map point during a cardiac cycle, defined by the PS motion data. For example, the motion waveforms may be temporally equalized by "stretching" the motion waveforms that have shorter cycle lengths until the shorter motion waveform subsets have a length equal to a predetermined or common time interval. The common time interval may be predetermined, or automatically selected, such as by choosing a length corresponding to the longest, shortest, or average length of the motion waveforms define by the PS motion data within the point cloud data set. The time interval may be set to begin at a point in time defined by a global signal such as the peak of the R-wave as detected by using the Electrocardiogram (ECG) or Intracardiac Electrogram (IEGM) signals as disclosed in the U.S. Provisional Application No. 61/910,630. Optionally, the time interval may be defined to begin based on another global marker of electrical activity (e.g., the T-wave, P-wave).

Figure 4:
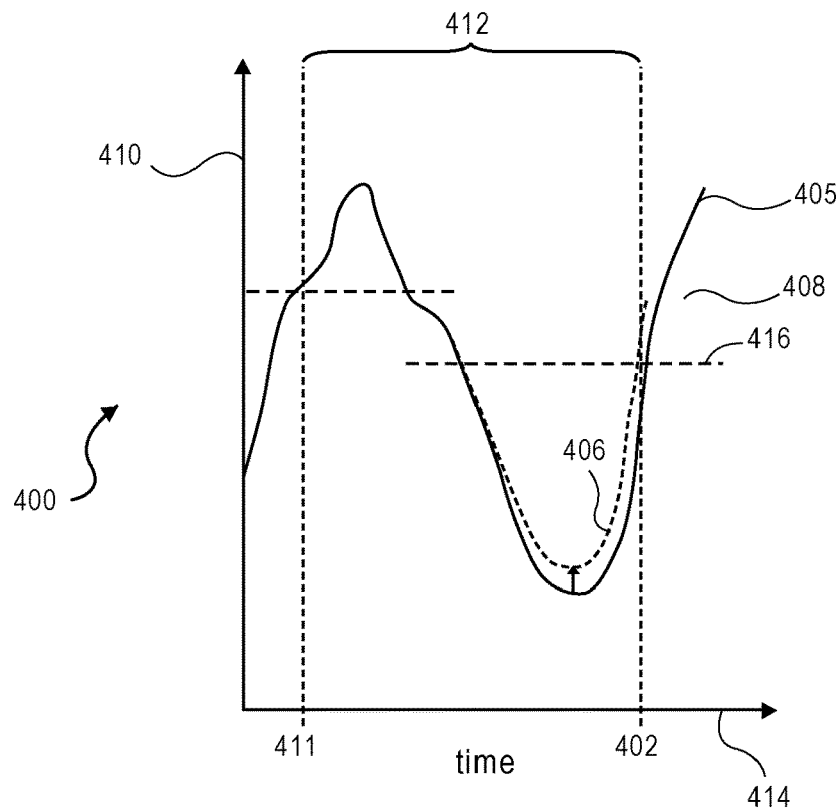
FIG. 4 illustrates a motion waveform associated with a map point being rotated in accordance with an embodiment herein.

Additionally or alternatively, the navigation system 120 may apply a rotation technique to the motion waveform to correct for non-periodicity. A periodic motion waveform of a map point during the cardiac cycle has, at the beginning and end of the cardiac cycle, approximately the same measured displacement or position. Non-periodicity may occur from errors in the acquired PS motion data for the map point that defines the motion waveform. For example, if the electrophysiological sensor 152 is not directly against the heart wall during the entire cardiac cycle the PS motion data may drift. FIG. 4 illustrates a graph illustration 400 of the motion waveform 405 defined by a plurality of PS motion data within the point cloud data set acquired at a map point (e.g., the map point 308). The motion waveform 405 may represent a displacement of the map point with respect to a vertical axis 410, representing an amount of displacement of the map point, during a cardiac cycle 412 along a horizontal axis 414. At a start 401 of the cardiac cycle 412, the motion waveform 405 has a measured displacement at 408. At an end 402 of the cardiac cycle 412, the motion waveform 405 has a measured displacement at 416. The difference in the displacements of the motion waveform 405 at the start 401 and the end 402 of the cardiac cycle 412 shows that the motion waveform 405 is non-periodic. The rotation technique may be applied to generate a rotated motion waveform 406 that results in a periodic motion waveform as disclosed in U.S. Provisional Application No. 61/910,630.

Additionally or alternatively, the navigation system 120 may average the PS motion data within the point cloud data set that correspond to a map point (e.g., the map point 308) measured over a plurality of cardiac cycles to determine an average motion waveform for the map point as disclosed in U.S. Provisional Application No. 61/906,305. For example, the motion waveform may be combined through averaging or otherwise. Optionally, the PS motion data, which is utilized in connection with embodiments described hereafter, may include information indicative of a radial component of wall movement, and/or may include information indicative of a longitudinal component of wall movement. Optionally, the motion data may include information associated with 3-dimensional (3-D) movement calculated as a (3-D) distance from an initial position at a select starting point in the cardiac cycle, such as an R-wave or local electrical activation time.

At 204, the method designates anatomic landmarks by defining apical, basal, and circumferential landmarks within the point cloud data set. The anatomical landmarks may be designated through manual operations by the user. Additionally or alternatively, the anatomical landmarks may be designated through automatic calculations based on analysis of the point cloud data set, for example, as described in U.S. patent application No. 14/270,194, titled "METHOD AND SYSTEM TO AUTOMATICALLY ASSIGN MAP POINTS TO ANATOMICAL SEGMENTS AND DETERMINE MECHANICAL ACTIVATION TIME", published as U.S. Pub. No. 20150317448, which is filed on the same day as the present application and which is expressly incorporated herein by reference in its entirety. The landmarks are located at various locations based upon the shape and nature of the region of interest. For example, at least one landmark is located proximate to, or at, the apex of the region of interest. Another landmark is located at, or proximate to, a middle of a base of the region of interest, while another landmark is located circumferentially from the base at an outer limit of the region of interest. For example, when the region of interest represents the right or left ventricle, the apex landmark represents the apex of the RV or LV. The basal landmark represents the base of the RV or LV and the circumferential landmark represents the left or right ventricular outflow tract.

One or more axes may be defined from the landmarks. For example, a long axis of the RV or LV is defined as a line connecting the apex to the basal point/landmark. A circumferential line is drawn from the basal landmark to the circumferential landmark. The long axis and circumferential line are used to position and orient a transformation coordinate system. For example, the long axis may be used as a Z-axis and the circumferential line is used as the circumferential line of the cylindrical coordinate system. The long axis and circumferential line are used as a basis to convert the point data from a base coordinate system, such as the Cartesian coordinate system, to a coordinate system associated with the regions of interest. For example, location coordinates for point data may be converted from XYZ Cartesian coordinates to longitudinal, radial, and circumferential coordinates of the cylindrical coordinates.

At 206, the method 200 automatically calculates circumferential segment boundaries, within the point cloud data set, based on the apical, basal and circumferential landmarks.

At 208, the method 200 assigns map points to the circumferential segments as defined at 206. In order to automatically assign each map point, the method determines a corresponding segment of the anatomical map. To do so, in at least one embodiment, the method defines a reference line between the basal landmark and circumferential landmark. The circumferential location of each map point (θm) at a predefined point in the cardiac cycle, such as at the peak of the QRS complex, is compared against the circumferential landmark (θLVOT). A tolerance may be used such as (θLVOT−π/6−tolerance)≤☐m≤(θLVOT+π/6+tolerance). Each map point is assigned to the corresponding wall segment, where the circumferential landmark is used to identify a reference wall segment, such as the anteroseptal wall segment. Upon definition of the segment boundaries of the first wall segment with the option of including a circumferential tolerance on the order of π/36, the definitions of the other wall segments include the subsequent addition or subtraction of multiples of (π/3+tolerance) until the entire circumference of a region of interest (e.g, LV) is assigned to the appropriate wall segment.

Additionally or alternatively, the navigation system 120 may convert the map points from Cartesian coordinates to a cylindrical coordinate system (e.g., r, θ, Z) when assigning the map points. Various techniques may be used for transforming between the Cartesian and cylindrical coordinate systems. Alternative base coordinate systems may be used instead of the Cartesian coordinate system. Optionally, the map points may be converted to an alternative coordinate system other than the cylindrical coordinate system. For example, the map points may be transformed to the spherical, polar or another system.

At 210, the method calculates the longitudinal segment boundaries. At 212, the method assigns map points to the longitudinal segments based on the longitudinal segment boundaries. For example, the method performs segmentation along the long axis for definition of apical vs. midventricular vs. basal points. The longest available length of the long axis ($L_{Long\ Axis}$) is determined. An apical portion (AP) parameter is then defined which determines the extent of the apical segments and $L_{Long\ Axis}$ is divided by AP, such that any point with a longitudinal coordinate less than L/AP is assigned to the apex. A typical value for AP may be 3, in which the apical segments cover ⅓ of the length of the entire wall from apex to base. Next, the remaining points with longitudinal coordinates less than $$\frac{L_{LongAxis}(AP+1)}{2AP}$$

are assigned to the mid-ventricular segments and those with longitudinal coordinates more than this value are assigned to the basal segments. A longitudinal tolerance can also be introduced to allow for some flexibility in this assignment.

At 214, the map points are stored in a data storage (e.g., ROM 1404, RAM 1406, hard drive 1408) with associated segment assignments. Additionally or alternatively, the navigation system 120 may calculate circumferential and longitudinal segment boundaries, for the point cloud data set, based on the apical, basal and circumferential landmarks as disclosed in U.S. patent application No. 14/270,191, titled "METHOD AND SYSTEM TO AUTOMATICALLY ASSIGN MAP POINTS TO ANATOMICAL SEGMENTS AND DETERMINE MECHANICAL ACTIVATION TIME", published as U.S. Pub. No. 20150317448.

FIG. 5 illustrates a three dimensional (3D) visualization 500 of map points 510 located at the LV 530 with associated segments 520 from the point cloud data set, which may be shown on the display 158, based on the method 200 described above. FIG. 5 illustrates the left ventricular 530 of the heart divided into segments (not all segments shown) 520 formed from, for example, 6 circumferential segment boundaries 512 (not all divisions shown) and 3 longitudinally segment boundaries 514. It should be noted in alternative embodiments the number of circumferential and longitudinal segments may be fewer than or greater than shown in FIG. 5. Optionally, the three dimensional visualization 500 may include a graphical marker for an apical landmark 502, a basal landmark 506, and circumferential landmarks (e.g., septal, anterior-septal, anterior) 504. The map points 510 are assigned to an associated segment 520 based on the location of the map points 510. For example, the map points 510a-c are associated with the segment 520a based on the map points 510a-c positioned within the segment 520a.

Additionally or alternatively, the map points (as described above) may be based on a cylindrical coordinate system. For example, the map points 510 may be oriented based on a longitudinal axis 522, a polar or radial axis 524 with an origin approximate to the apex 502, and an angular coordinate or azimuth from the radial axis 524 in the direction of the an arrow 526. It should be noted, in alternative embodiments the coordinate system may be oriented or have an origin on other landmarks within the region of interest, for example, the base, septal, or the like. Optionally, the coordinate system may be oriented or have an origin external to the region of interest (e.g., the heart), for example based on a reference external to the patient such as the transmitter assembly 150 of the CNS 110.

Optionally, a subset of the map points 510 may be assigned to multiple segments 520 based on the distance of the map points 510 from at least one of the longitudinal and/or circumferential segment boundaries 512 and 514. For example, the map points 510*d-e* may be associated to both the segments 520*b-c* based on being proximate to the circumferential segment boundary 512*a*.

Based on the position of two or more map points during the cardiac cycle, the navigation system 120 may determine a strain within the segment, the wall of the LV and/or RV, or the like. Strain is a measure of tissue deformation, and is defined as the change in length of the tissue normalized with respect to an original length. There may be three primary directions of strain in the heart tissue: a longitudinal direction (e.g., traversing along the longitudinal axis 522 or the $L_{Long\ Axis}$), a radial direction (e.g., traversing along the radial axis 524), and/or a circumferential direction (e.g., traversing along the arrow 526). The navigation system 120 may use Equation 1 to determine the linear strain (the variable) between two map points or reference locations during the cardiac cycle.

The term reference locations is used throughout to refer to a tissue or wall segment ends. Pairs of reference locations are used to designate opposite ends of a tissue or wall segment for which strain is measured. The reference locations may, but need not, correspond to individual map points.

The variable of Equation 1 represents an instantaneous distance between the two reference locations at a moment of time during the cardiac cycle. The variable of Equation 1 represents a reference distance between the two reference locations at a pre-defined temporal reference or time during the cardiac cycle. For example, the pre-defined temporal reference may be a time corresponding to a peak of the surface ECG R-wave. It should be noted that the distance between the two reference locations may be based on the space in time (e.g. based on the cardiac cycle) of the two reference locations, the spatial separation between the two references irrespective of the mapping sequences, or the like.

$$\varepsilon = \frac{d - d_o}{d_o} \quad \text{(Equation 1)}$$

Equation 1 may be used by the navigation system 120 to determine other types of strain such as radial strain, and/or circumferential strain. The type of strain is dependent on the direction of the distances represented as $d$ and $d_o$. For example, for radial strain, the distance (e.g., $d$ and $d_o$) is the distance between endocardial and epicardial references directly transmurally placed from one another. For circumferential strain, the distance (e.g., $d$ and $d_o$) is the difference in the circumferential angle or distance (in relation to the arrow 526) between the two reference locations in radians.

For linear strain, the longitudinal distance (e.g., $d$ and $d_o$) between the two reference locations may be determined according to Equation 2 below. The variable $z_1(t)$ and $z_2(t)$ are the longitudinal positions of each of the reference locations during the cardiac cycle.

$$d = z_2(t) - z_1(t) \quad \text{(Equation 2)}$$

Additionally or alternatively, distance (e.g., $d$ and $d_o$) between two reference locations, with positions based on Cartesian coordinates, may be determined accord to Equation 3 below $$d = (\sqrt{(x_1-x_2)^2 + (y_1-y_2)^2 + (z_1-z_2)^2} \quad \text{(Equation 3)}$$

Figure 13:
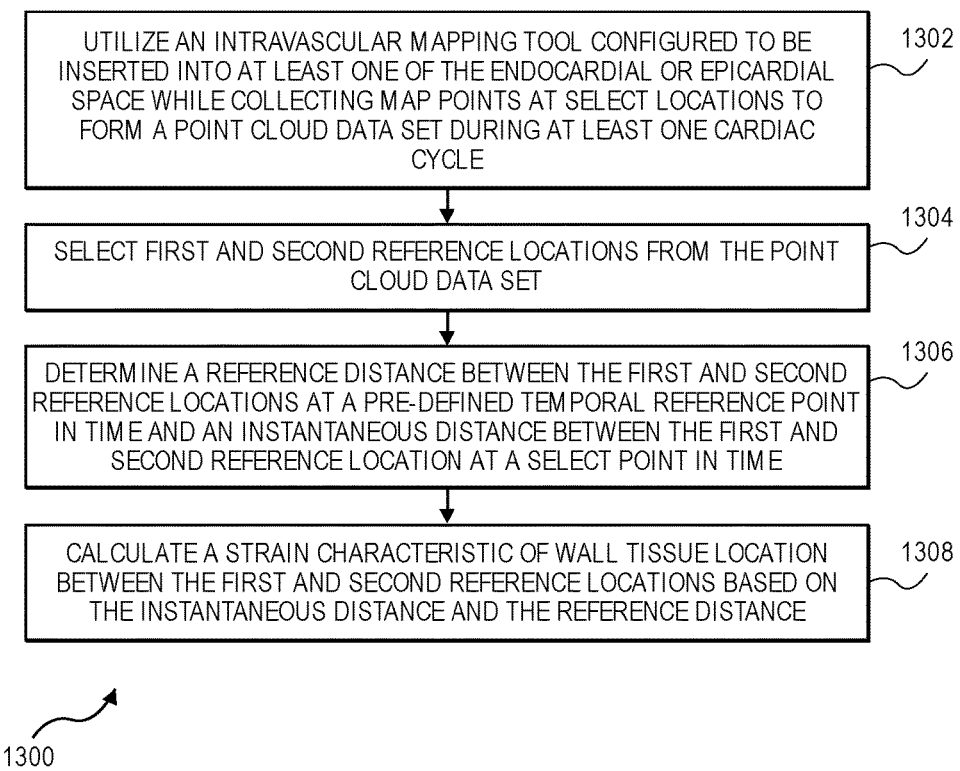
FIG. 13 illustrates a method performed in accordance with embodiments herein for calculating a strain from characterization motion data.

FIG. 13 illustrates a flowchart of a method 1300 for calculating a strain from characterization motion data. The method 1300, for example, may employ structures or aspects of various embodiments (e.g., systems and/or methods) discussed herein (e.g., the CNS 110 in FIG. 1). In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. It should be noted, other methods may be used, in accordance with an embodiment herein.

At 1302, the method 1300 utilizes an intravascular mapping tool configured to be inserted into at least one of the endocardial or epicardial space while collecting map points at select locations to form a point cloud data set during at least one cardiac cycle as explained in connection with FIG. 3.

At 1304, the method 1300 selects first and second reference locations in the point cloud data set. For example, the navigation system 120 or the clinician via the operator system interface 154 may select two reference locations such as two map points (e.g., 602*a-b*). The map points may be selected based on the longitudinal distance of the map points (e.g., furthest longitudinal distance) as described in relation to FIGS. 6-7. Additionally or alternatively, the navigation system 120 or the clinician may select at least two reference locations and/or based on the longitudinal alignment of the reference locations based on the circumferential position of the reference locations. Optionally, the navigation system 120 or the clinician may select at least two reference locations based as described in relation to FIGS. 8-12.

At 1306, the method determines a reference distance between the first and second reference locations at a pre-defined temporal reference point and an instantaneous distance between the first and second reference location at a select point in time.

At 1308, the method 1300 calculates a strain based on an instantaneous distance and a reference distance between the first and second reference locations (determined at 1306). For example the navigation system 120 may determine the strain of the first and second reference locations based on Equations 1 and 2 as described in relation to FIGS. 7, 9, and 12.

Figure 6:
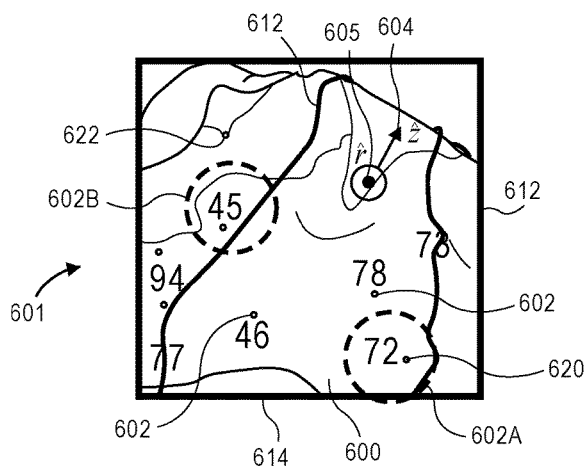
FIG. 6 illustrates a segment within a three dimensional visualization of map points from a point cloud data set, in accordance with an embodiment herein.
Figure 8:
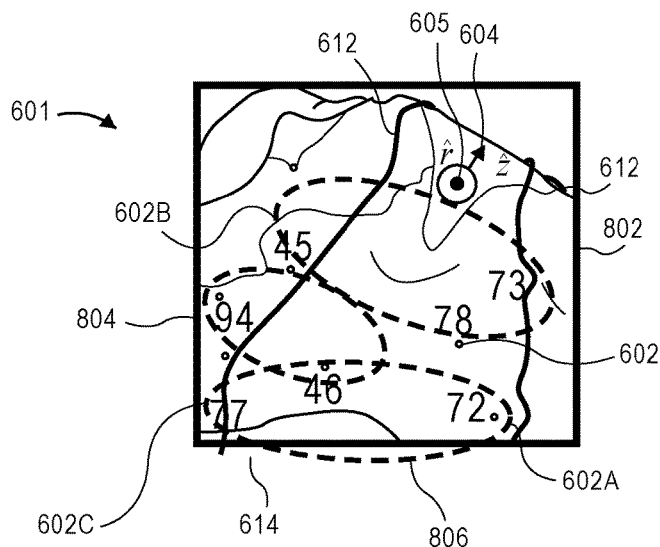
FIG. 8 illustrates a segment within a three dimensional visualization of map points from a point cloud data set, in accordance with an embodiment herein.

FIGS. 6 and 8 illustrate a segment 600 within a three dimensional (3D) visualization 601 of map points 602 from a point cloud data set of the LV. The segment 600 is bounded by circumferential segment boundaries 612 and longitudinal segment boundaries 614. A vector arrow 604 indicates the direction of the z or longitudinal axis (e.g., the longitudinal axis 522) based on a cylindrical coordinate system oriented or having an origin on or about the apex (not shown). Further, a vector arrow 605 indicates the direction of the r or radial axis (e.g., the radial axis 524). Optionally, the clinician may view the 3D visualization 601 on the display 158.

To determine the linear strain within the segment 600, the navigation system 120 may select two map points or reference locations with the farthest longitudinal positions within the segment 600. For example, the navigation system 120 may calculate the reference distance, $d_o$, between every pair of map points 602 within the segment 600 at the pre-defined temporal reference 708 such as the time corresponding to a peak of the surface ECG signal. Additionally or alternatively, the navigation system 120 may determine an average distance between every pair of map points 602 over the cardiac cycle from Equation 2. It should be noted, that in embodiments strain may be determined between reference locations not within the same segment (e.g., description regarding FIGS. 10-12), between opposing segments (e.g., the segment 520 and the opposing segment (not shown), between wall regions (e.g., the apex 502 and the base 506), or the like.

Figure 7:
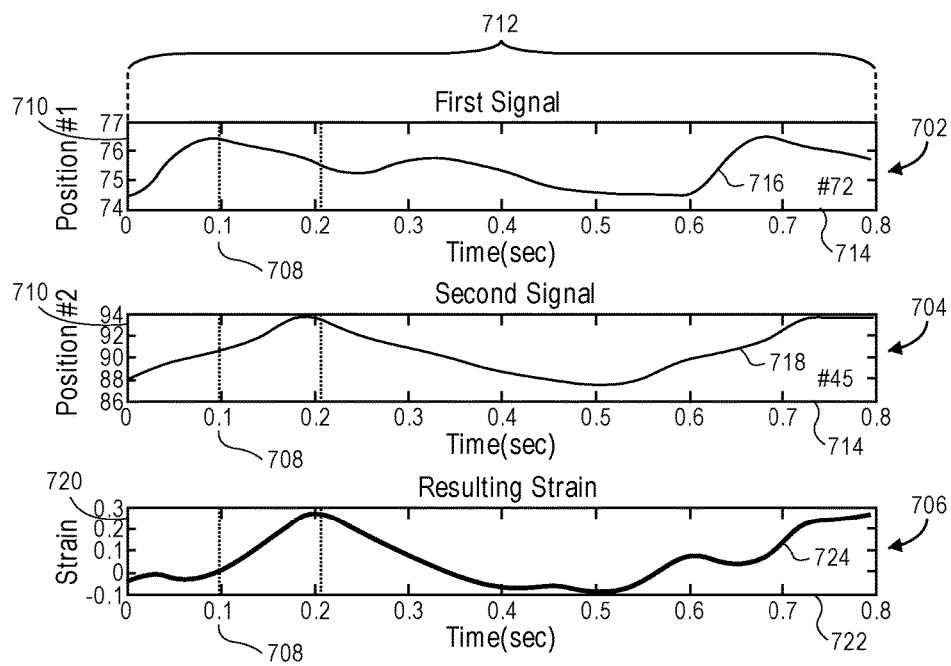
FIG. 7 illustrates two positional graphs and a strain graph based on two reference locations from FIG. 6, in accordance with an embodiment herein.

FIG. 7 illustrates two positional graphs 702 and 704 based on two reference locations, specifically the map point 602a and the map point 602b respectively (graphically highlighted by dashed circles 620 and 622 in FIG. 6). The two reference locations may have been selected by the navigation system 120, as described above, with the farthest longitudinal positions within the segment 600 relative to the remaining possible pairs of map points 602. The two positional graphs 702 and 704 show the longitudinal position 716, 718 (e.g., $z_2(t)$ and $z_1(t)$ respectively) of the respective map points 602a, 602b along vertical axes 710 with respect to time, which is represented along horizontal axes 714. The horizontal axes 714 illustrate the duration of a cardiac cycle 712. The longitudinal position of the map points 602a, 602b is based on the longitudinal distance of the map points 602a, 602b from the apex (not shown) or the origin of the cylindrical coordinate system.

FIG. 7 further illustrates a strain graph 706 based on two reference locations, namely, the map points 602a, 602b. The strain waveform 724 (e.g.,$\varepsilon$) is determined from Equation 1 and shown along the vertical axis 720 with respect to time, which is represented along the horizontal axis 722. It should be noted, that the strain waveform 724 at the pre-defined temporal reference 708 is zero. Since the distance between the map points 602a, 602b at the reference distance and the instantaneous distance is equal at the pre-defined temporal reference 708, the heart wall tissue between map points 602a, 602b does not undergo any strain 724.

Optionally, the strain waveform 724 may be rotated similar to the motion waveform described above to ensure periodicity. It should be noted that in embodiments at least one of the reference locations used to determine strain may be outside of the segment 600 to determine a strain of a larger region. For example, one of the reference locations may be located at the septal or lateral wall of the LV, to determine a wall strain from the two reference locations.

Additionally or alternatively, the navigation system 120 may determine the linear strain of the segment 600 based on two longitudinally-aligned reference locations with the farthest longitudinal positions within the segment 600. The navigation system 120 may determine the longitudinal alignment of two reference locations based on the difference in circumferential position of the two reference locations, relative to each other. The difference in circumferential positions may be determined from the average circumferential distance between every pair of reference locations (e.g., map points 602) within the segment 600. Alternatively, the navigation system 120 may determine the circumferential distance between every pair of reference locations within the segment 600 at the pre-determined temporal reference 708. Once a set of paired longitudinally-aligned reference locations are determined, the navigation system 120 may determine which of the paired reference locations have the farthest longitudinal positions within the segment 600, as described above, which will be used to calculate the linear strain of the segment 600.

Additionally or alternatively, the navigation system 120 may determine the linear strain of the segment 600 by sub-segmenting the segment 600 in two or more longitudinal sub-segments (e.g., 802, 804, 806). The longitudinal sub-segments 802, 804, 806 each include a set of unique map points 602. Optionally, the clinician through the operator user interface 154 may set the position, number, and/or size of the longitudinal sub-segments within the segment 600.

In embodiments, the position of the map points 602 along the direction 604 of the longitudinal axis may determine the corresponding longitudinal sub-segment 802, 804, 806 with the map point. FIG. 8 illustrates three longitudinal sub-segments within the segment 600, an apical sub-segment 806, a mid sub-segment 804, and a base sub-segment 802. Each of the sub-segments 802, 804, 806 are positioned based on a distance along the longitudinal axis. For example, the apical sub-segment 806 is positioned proximate to the apex (not shown) or at a position lower along the longitudinal axis compared to the remaining longitudinal sub-segments 802, 804. The mid sub-segment 804 is positioned between the apical and base sub-segments 806 and 802. The base sub-segment 802 is positioned furthest away from the apex (not shown) or at a distal end of the Di having a position greater along the longitudinal axis compared to the remaining longitudinal sub-segments 804, 806.

Optionally, the size of the longitudinal sub-segments 802, 804, 806 may be based on a longitudinal position bandwidth. For example, the length of the longitudinal boundary 612 along the longitudinal axis defining the segment may be divided equally to define longitudinal boundaries of the longitudinal sub-segments 802, 804, 806. In embodiments, the size of the longitudinal sub-segments 802, 804, 806 may be increased to allow a set minimum number of map points 602 within longitudinal sub-segment 802, 804, 806.

In embodiments, the navigation system 120 may determine an average longitudinal position waveform for each longitudinal sub-segment 802, 804, 806 based on the position waveforms of the map points 602 within the corresponding longitudinal sub-segment 802. For example, the average longitudinal position waveform for the apical sub-segment 806 is the average of the position waveforms of the map points 602a and 602c positioned within the apical sub-segment 806.

Figure 9:
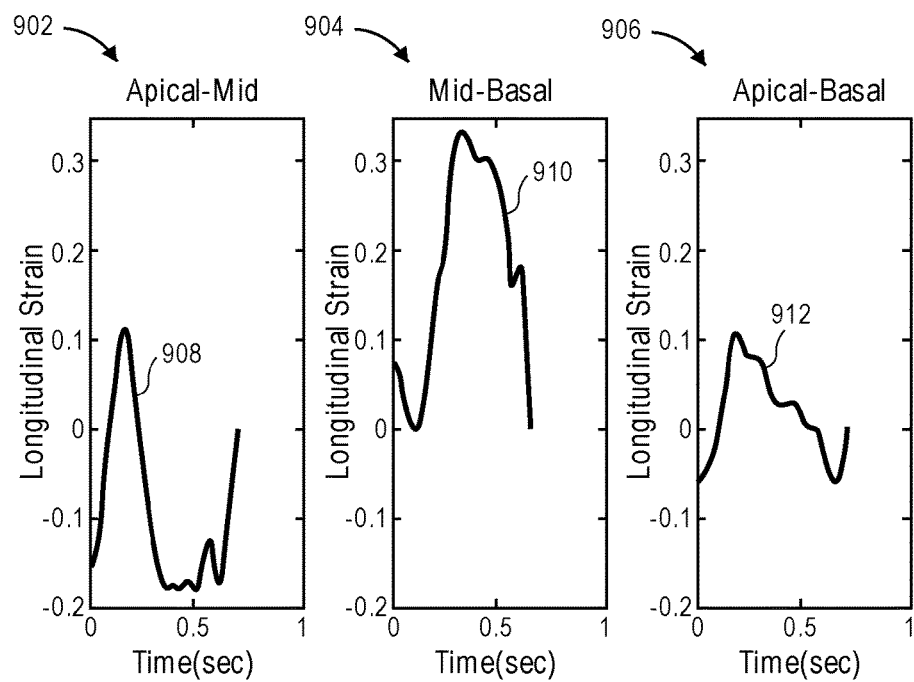
FIG. 9 illustrates three strain graphs based on three reference locations from FIG. 8, in accordance with an embodiment herein.

The average longitudinal position waveforms may be used to determine a linear strain between two of the longitudinal sub-segments 802, 804, 806 using Equations 1 and 2 based on a pre-determined temporal reference 914. FIG. 9 illustrates three strain graphs 902, 904, 906 based on the three longitudinal sub-segments 802, 804, 806. The strain graph 902 illustrates a strain waveform 908 that represents the linear strain between the apical sub-segment 806 and the mid sub-segment 804. The strain graph 904 illustrates a strain waveform 910 that represents the linear strain between the basal sub-segment 802 and the mid sub-segment 804. The strain graph 906 illustrates a strain waveform 912 that represents the linear strain between the apical sub-segment 806 and the basal sub-segment 802.

The navigation system 120 may determine a linear strain of the segment 600 by averaging the linear strain waveforms 908, 910, and 912. Optionally, the navigation system 120 may determine the linear strain of the segment 600 by selecting the linear strain waveforms determined from two linear sub-segments (e.g., 802 and 806) having the furthest longitudinal distance from each other within the segment 600. For example, the navigation system 120 may select the linear strain waveform 912 defined by the apical sub-segment 806 and the basal sub-segment 802. The apical sub-segment 806 positioned proximate to the apex and the basal sub-segment 802 positioned proximate to the basal end of the LV have the greatest longitudinal distance from each other.

It should be noted, that sub-segmenting may be performed on larger regions of interest relative to the segment 600. For example, the entire septal or lateral wall of the LV may be sub-segmented using the process described above, which may be used to determine a linear strain of the wall.

Figure 10:
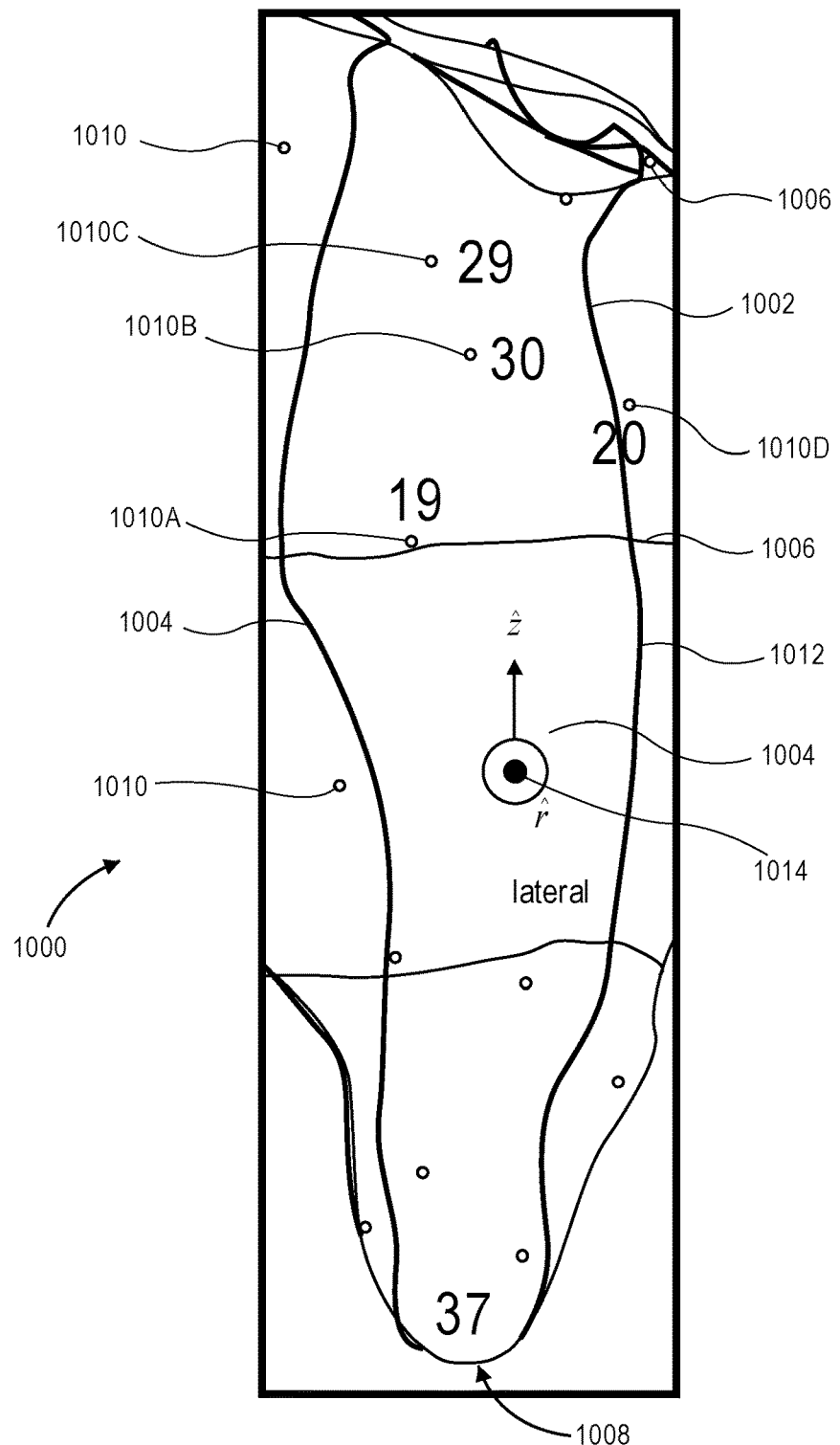
FIG. 10 illustrates map points within a segmented left ventricular, in accordance with an embodiment herein.

Additionally or alternatively, the navigation system 120 may determine the linear strain of a segment 1002 based on an internal reference location (e.g., an RV apex, an LV apex 1008). FIG. 10 illustrate 3D visualization 1000 of a point cloud data of the LV. The segment 1002 is bounded by circumferential segment boundaries 1006 and longitudinal segment boundaries 1004. A vector arrow 1012 indicates the direction of the z or longitudinal axis (e.g., the longitudinal axis 522) based on a cylindrical coordinate system oriented or having an origin on or about the apex 1008 at a pre-determined coordinate temporal reference. The pre-determined coordinate temporal reference may be determined by the clinician using the operator user interface 154. The pre-determined coordinate temporal reference is used to have the origin of the coordinate system (e.g., the cylindrical coordinate system) static even though the position of the apex 1008, which may be used as an origin landmark, moves during the cardiac cycle. A vector arrow 1014 indicates the direction of the 'r' or radial axis (e.g., the radial axis 524). In embodiments, the clinician may view the 3D visualization 1000 on the display 158. Additionally or alternatively, the navigation system 120 may determine strain within a branch of the coronary sinus on the epicardial surface relative to an internal reference.

Figure 11:
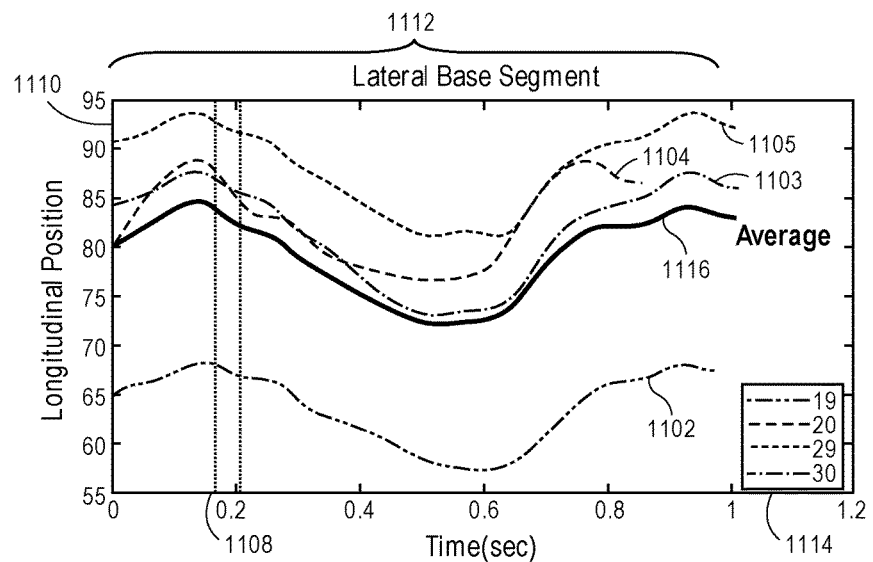
FIG. 11 illustrates a position graph of map points within a segment of FIG. 10, in accordance with an embodiment herein.

FIG. 11 illustrates longitudinal position waveforms 1102-1105 based on the map points 1010a-d within the segment 1002. The longitudinal position waveforms 1102-1105 show the longitudinal position of the respective map points 1010a-d during a cardiac cycle 1112 along a vertical axis 1110 and a horizontal axis 1114 representing time. The longitudinal position of the map points 1010a-d is based on the longitudinal distance of the map points 1010a-d from the apex 1008 along the longitudinal axis at the pre-determined coordinate temporal reference 1108. The navigation system 120 may determine an average longitudinal position waveform 1116 based on the positional waveforms 1102-1105.

Figure 12:
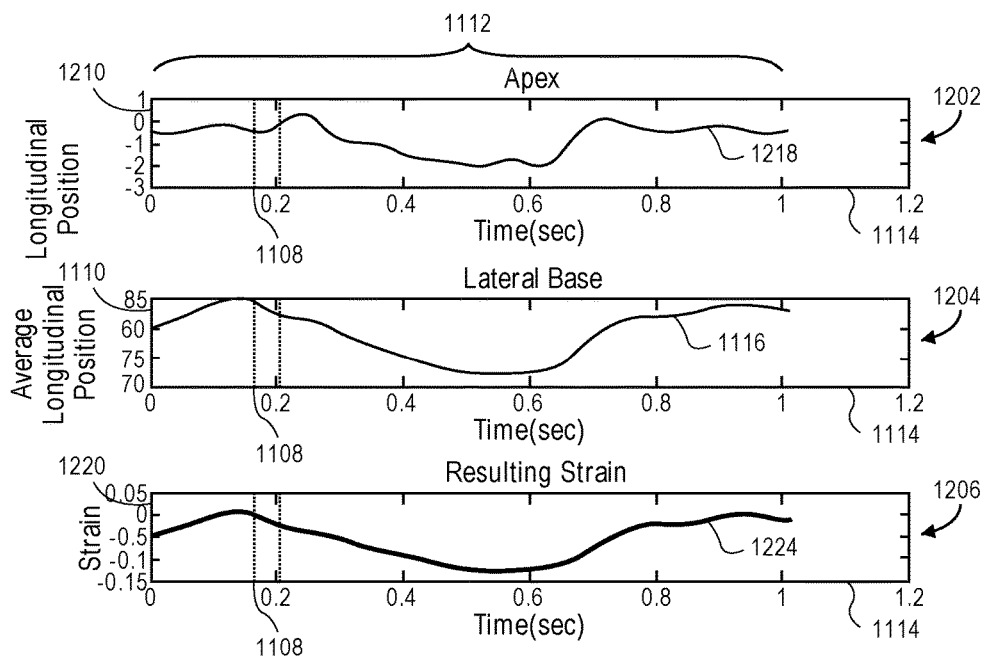
FIG. 12 illustrates two positional graphs and a strain graph based on two reference locations from FIG. 10, in accordance with an embodiment herein.

FIG. 12 illustrates two positional graphs 1202 and 1204 based on the apex 1008 and the map points 1010a-d within the segment 1002, respectively. The positional graph 1204 shows the average longitudinal position waveform 1116 as described above. The positional graph 1202 shows the longitudinal position waveform 1218 during the cardiac cycle 1112 along a vertical axis 1210 and the horizontal axis 1114. The longitudinal position of the apex 1008 is based on the longitudinal distance of the apex 1008 from the longitudinal position of the apex 1008 at the pre-determined coordinate temporal reference.

FIG. 12 further illustrates a strain graph 1206 based on the average longitudinal position waveform 1116 and the longitudinal position waveform 1218. The strain waveform 1224 (e.g., ε) may be determined by the navigation system 120 from Equation 1. The strain waveform 1224 is illustrated along a vertical axis 1220 with respect to the horizontal axis 1114. The strain waveform 1224, based on the average longitudinal position waveform 1116, is a representative strain curve for the segment 1002.

In embodiments, the navigation system 120 may determine strain waveforms for each map point 1010a-d by severally determining a strain waveform based on the longitudinal position waveforms 1102-1105 and the longitudinal position waveform 1218. Optionally, the representative strain curve for the segment 1002 may be determined by averaging the strain waveforms for each map point 1010a-d.

Optionally, the navigation system 120 may determine strain within a branch of the coronary sinus on the epicardial surface. For example, the two reference locations may be determined based on the anatomy of the coronary sinus and/or the presence of the branch between the two reference points.

Additionally or alternatively, the branch and/or segments of the branch of the coronary sinus may be divided in to sub-segments as described regarding FIGS. 8-9. For example, the number, size, and/or position of the sub-segments may be determined based on the anatomy of the coronary sinus and/or the presence of the branch within the segment.

Figure 14:
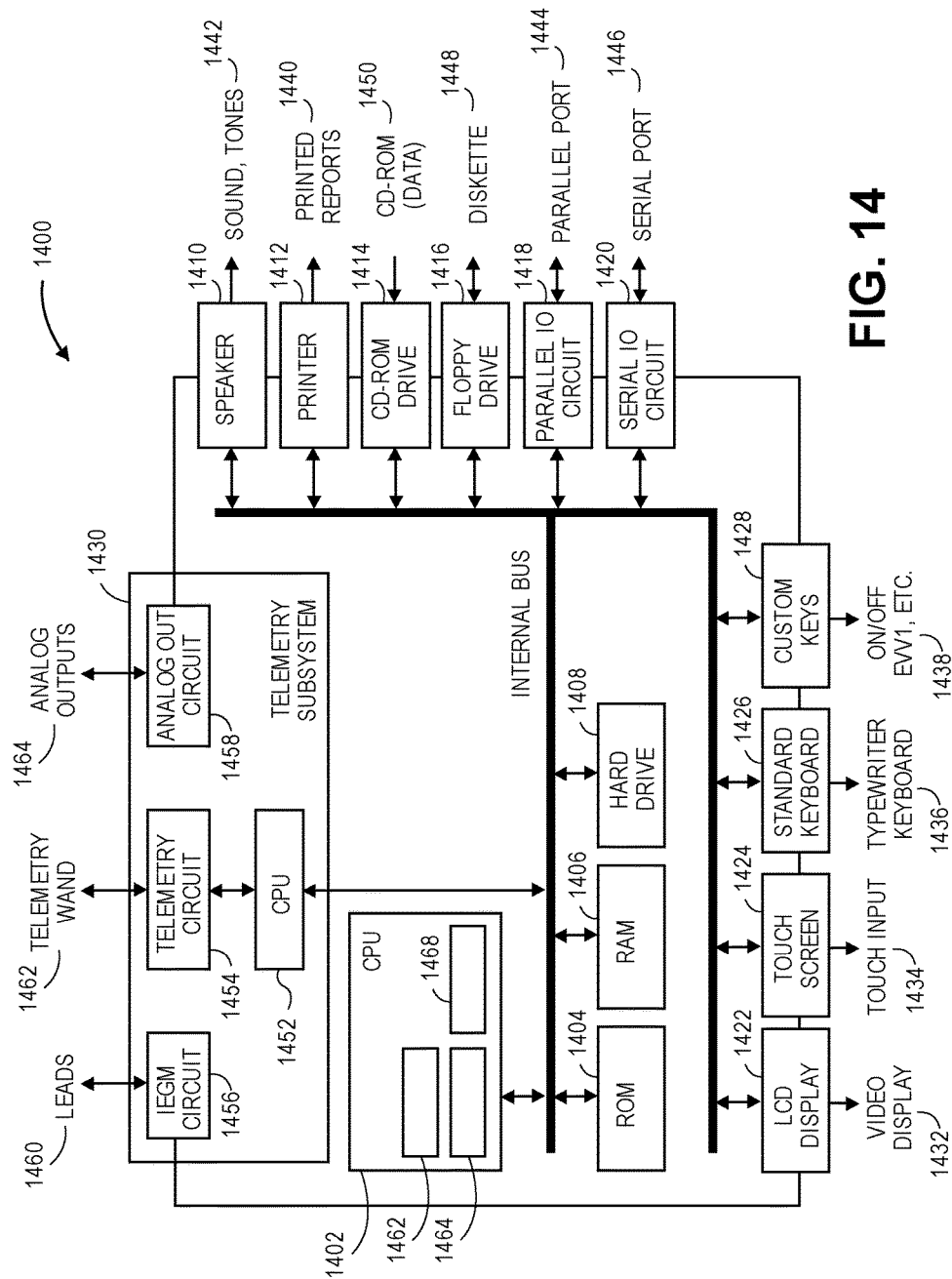
FIG. 14 illustrates a system for analyzing motion data in accordance with an embodiment.

FIG. 14 illustrates a functional block diagram of an embodiment of an electronic control unit (ECU) 1400 that is operated in accordance with the processes described herein to analyze motion data and to interface with the CNS 110. The ECU 1400 may be a workstation, a portable computer, a PDA, a cell phone and the like. The ECU 1400 includes an internal bus that connects/interfaces with a Central Processing Unit (CPU) 1402, ROM 1404, RAM 1406, a hard drive 1408, the speaker 1410, a printer 1412, a CD-ROM drive 1414, a floppy drive 1416, a parallel I/O circuit 1418, a serial I/O circuit 1420, the display 1422, a touch screen 1424, a standard keyboard connection 1426, custom keys 1428, and a telemetry subsystem 1430. The internal bus is an address/data bus that transfers information between the various components described herein. The hard drive 1408 may store operational programs as well as data, such as waveform templates and detection thresholds.

The CPU 1402 typically includes a microprocessor, a microcontroller, or equivalent control circuitry, and may interface with the CNS 110. The CPU 1402 may include RAM or ROM memory, logic and timing circuitry, state machine circuitry, and I/O circuitry to interface with the CNS 110. The display 1422 (e.g., may be connected to the video display 1432). The touch screen 1424 may display graphic information relating to the CNS 110. The display 1422 displays various information related to the processes described herein. The touch screen 1424 accepts a user's touch input 1434 when selections are made. The keyboard 1426 (e.g., a typewriter keyboard 1436) allows the user to enter data to the displayed fields, as well as interface with the telemetry subsystem 1430. Furthermore, custom keys 1428 turn on/gaff 1438 (e.g., EVVI) the ECU 1400. The printer 1412 prints copies of reports 1440 for a physician to review or to be placed in a patient file, and speaker 1410 provides an audible warning (e.g., sounds and tones 1442) to the user. The parallel I/O circuit 1418 interfaces with a parallel port 1444. The serial I/O circuit 1420 interfaces with a serial port 1446. The floppy drive 1416 accepts diskettes 1448. Optionally, the floppy drive 1416 may include a USB port or other interface capable of communicating with a USB device such as a memory stick. The CD-ROM drive 1414 accepts CD ROMs 1450.

The CPU 1402 is configured to analyze PS motion data collected by the CNS 110 for a plurality of map points to determine a point cloud data set of the map points stored on data storage (e.g., ROM 1404, RAM 1406, hard drive 1408). The CPU 1402 includes a segmentation analysis circuit module 1464 that is configured to automatically assign segment identifiers (IDs), which are associated with segments of the heart separated by circumferential and longitudinal boundaries, to the map points based on a position of the map point from the point cloud data set. The CPU 1402 also includes a position waveform generation circuit module 1462 that may generate position waveforms of selected reference locations based a coordinate system (e.g., Cartesian coordinate system, cylindrical coordinate system, or the like) as described herein. The CPU 1402 also includes a strain analysis circuit module 1468 that may determine the strain (e.g., linear or longitudinal strain, radial strain, circumferential strain), as explained herein.

The telemetry subsystem 1430 includes a central processing unit (CPU) 1452 in electrical communication with a telemetry circuit 1454, which communicates with both an IEGM circuit 1456 and an analog out circuit 1458. The circuit 1456 may be connected to leads 1460. The circuit 1456 may also be connected to implantable leads to receive and process IEGM cardiac signals. Optionally, the IEGM cardiac signals sensed by the leads may be collected by the CNS 110 and then transmitted, to the ECU 1400, wirelessly to the telemetry subsystem 1430 input.

The telemetry circuit 1454 is connected to a telemetry wand 1462. The analog out circuit 1458 includes communication circuits to communicate with analog outputs 1464. The ECU 1400 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 1400 to the CNS 110.

It should be noted that although the above embodiments may focus on strain calculations in the LV, it should be understood, by one in the art, that the above described techniques may also be applied to other chambers and other organs in which local biomechanical behavior is of interest. Additionally, it should be noted that although the above embodiments may focus on longitudinal strain, it should be understood by one in the art that the above described techniques may also be applies to radial positioned from endocardial and epicardial map points across the myocardial wall to obtain radial strain which is indicative of wall thickening. Similarly, circumferential positions can be used to obtain a measure of active twist during contraction.

It should be noted that although the above embodiments may focus on strain calculations using a cylindrical coordinate system, it should be understood, by one in the art, that the above described techniques may also be applied to two reference points based on a 3D distance (e.g., Cartesian coordinates) as shown in Equation 3. The use of the 3D distance allows the navigation system 120 to determine a distance between the two reference points in the absence of a predefined dimension such as longitudinal or circumferential.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

The methods herein may be implemented as a software algorithm, package, or system that directs one or more hardware circuits or circuitry to perform the actions described herein. For example, the operations of the methods herein may represent actions to be performed by one or more circuits that include or are connected with processors, microprocessors, controllers, microcontrollers, Application Specific Integrated Circuits (ASICs), Field-Programmable Gate Arrays (FPGAs), or other logic-based devices that operate using instructions stored on a tangible and non-transitory computer readable medium (e.g., a computer hard drive, ROM, RAM, EEPROM, flash drive, or the like), such as software, and/or that operate based on instructions.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein," Moreover, in the following claims, the terms "first," "second," and "third," etc, are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter and also to enable a person of ordinary skill in the art to practice the embodiments of the inventive subject matter, including making and using any devices or systems and performing any incorporated methods. The patentable scope of the inventive subject matter is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the inventive subject matter will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (for example, processors or memories) may be implemented in a single piece of hardware (for example, a general purpose signal processor, microcontroller, random access memory, hard disk, and the like). Similarly, the programs may be stand-alone programs, may be incorporated as subroutines in an operating system, may be functions in an installed software package, and the like. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the inventive subject matter are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The invention claimed is:

1. A method for calculating a strain from characterization motion data, the method comprising:
utilizing an intravascular mapping tool configured to be inserted into at least one of the endocardial or epicardial space, the mapping tool maneuvered to select locations proximate to surfaces of the heart, while collecting a group of map points at the select locations to form a portion of a point cloud data set during at least one cardiac cycle;
utilizing one or more processors, when executing programmable instructions, for:
selecting first and second reference locations from the point cloud data set, wherein the first and second reference locations include at least first and second map points, respectively, that are indicative of wall movement at local corresponding surfaces of the heart;
determining a reference distance between the first and second reference locations at a pre-defined temporal reference point in time, and an instantaneous distance between the first and second reference locations at a select point in time;
calculating a strain characteristic of wall tissue based on the wall movement at the local corresponding surfaces between the first and second reference locations using the formula:

$$\varepsilon = \frac{d - d_o}{d_o},$$

wherein d is the instantaneous distance and $d_o$ is the reference distance; and displaying strain information in connection with identifying a location for lead placement, the strain information representing the strain characteristic of wall tissue located between the first and second reference locations.

2. The method of claim 1, wherein the second reference location corresponds to an internal reference location, the first reference location including multiple map points of the group of map points that are within a first wall segment identifier (ID).

3. The method of claim 2, further comprising calculating an average strain based on multiple calculated strains, wherein the strain is calculated individually for each of the map points of the first reference location.

4. The method of claim 2, further comprising calculating an average position of the map points of the group of map points, wherein the first reference location is the average position.

5. The method of claim 1, wherein the displaying comprises displaying a strain graph as the strain information in connection with identifying the location for lead placement, the strain graph illustrating a strain waveform representing the strain characteristic.

6. The method of claim 5, further comprising calculating the reference distances between each of the map points within the group of map points, wherein the reference distance between the first and second map points is greater than the reference distances between the remaining map points within the group of map points.

7. The method of claim 5, wherein the selection of the first and second reference location is at least partially based on having circumferential positions of the first and second map points within a predetermined threshold.

8. The method of claim 5, further comprising calculating an average distance between each of the map points of the group of map points during the cardiac cycle, wherein the average distance between the first and second map points is greater than the average distances between the remaining map points within the group of map points.

9. The method of claim 5, wherein the first and second reference locations each include a plurality of map points, the instantaneous distance and the reference distance is based on an average position of the first and second reference locations.

10. The method of claim 1, further comprising automatically assigning segment identifiers (IDs) to the map points based on a position of the map point within the point cloud data set, the segment IDs are associated with segments of the heart where the segments are separated by circumferential and longitudinal boundaries.

11. The method of claim 1, wherein the select locations proximate to surfaces of the heart are within a branch of the coronary sinus on the epicardial surface.

12. A system for calculating a strain from characterization motion data, the system comprising:
a data storage configured to store a group of map points collected by an intravascular mapping tool configured to be inserted into at least one of the endocardial or epicardial space, the mapping tool maneuvered to select locations proximate to surfaces of the heart, while collecting the group of map points at the select locations to form a point cloud data set during at least one cardiac cycle;
a processor configured to:
determine a reference distance between first and second reference locations at a pre-defined temporal reference point in time, and an instantaneous distance between the first and second reference locations at a select point in time, wherein the first and second reference locations include at least first and second map points, respectively, that are indicative of wall movement at local corresponding surfaces of the heart; and automatically calculate a strain characteristic of wall tissue based on the wall movement at the local corresponding surfaces between the first and second reference locations using the formula:

$$\varepsilon = \frac{d - d_o}{d_o},$$

wherein d is the instantaneous distance and $d_o$ is the reference distance; and a display configured to display strain information in connection with identifying a location for lead placement, the strain information representing the strain characteristic of wall tissue located between the first and second reference locations.

13. The system of claim 12, wherein the second reference location corresponds to an internal reference location, the first reference location including multiple map points that are within a first wall segment.

14. The system of claim 13, wherein the processor is further configured to automatically calculate an average strain based on multiple calculated strains, wherein the strain is calculated individually for each of the map points of the first reference.

15. The system of claim 12, wherein the instantaneous distance and the reference distance is based on longitudinal positions of the first and second references.

16. The system of claim 12, wherein the display is configured to display a strain graph as the strain information in connection with identifying the location for lead placement, the strain graph illustrating a strain waveform representing the strain characteristic.

17. The system of claim 16, wherein the processor is further configured to calculate the reference distances between each of the map points within the group of map points, wherein the reference distance between the first and second map points is greater than the reference distances between the remaining map points within the group of map points.

18. The system of claim 16, wherein the selection of the first and second reference locations is at least partially based on having circumferential positions of the first and second map points within a predetermined threshold.

19. The system of claim 16, wherein the processor is further configured to calculate an average distance between each of the map points within the group of map points during the cardiac cycle, wherein the average distance between the first and second map points is greater than the average distances between the remaining map points within the group of map points.

20. The system of claim 16, wherein the first and second reference locations each include a plurality of map points, the instantaneous distance and the reference distance is based on an average position of the first and second reference locations.

* * * * *